(12) United States Patent
Molgaard-Nielsen et al.

(10) Patent No.: US 9,592,107 B2
(45) Date of Patent: Mar. 14, 2017

(54) VISUAL STABILIZER ON ANCHOR LEGS OF VENA CAVA FILTER

(71) Applicant: Cook Medical Technologies LLC, Bloomington, IN (US)

(72) Inventors: Arne Molgaard-Nielsen, Copenhagen (DK); Jacob Lund Clausen, Lyngby (DK); Per Hendriksen, Herlufmagle (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/945,725

(22) Filed: Nov. 19, 2015

(65) Prior Publication Data

US 2016/0067030 A1     Mar. 10, 2016

Related U.S. Application Data

(63) Continuation of application No. 13/521,458, filed as application No. PCT/US2011/020950 on Jan. 12, 2011, now Pat. No. 9,308,066.

(Continued)

(51) Int. Cl.
*A61M 29/00* (2006.01)
*A61F 2/00* (2006.01)
(Continued)

(52) U.S. Cl.
CPC .............. *A61F 2/00* (2013.01); *A61F 2/01* (2013.01); *A61F 2002/016* (2013.01); *A61F 2002/30322* (2013.01); *A61F 2220/005* (2013.01); *A61F 2220/0016* (2013.01); *A61F 2220/0058* (2013.01); *A61F 2230/005* (2013.01);
(Continued)

(58) Field of Classification Search
CPC .... A61F 2002/30322; A61F 2250/0026; A61F 2002/016; A61F 2250/0098; A61F 2230/005; A61F 2220/0016
See application file for complete search history.

(56) References Cited

U.S. PATENT DOCUMENTS

| | | | |
|---|---|---|---|
| 5,059,205 | A | 10/1991 | El-Nounou et al. |
| 5,133,733 | A | 7/1992 | Rasmussen et al. |

(Continued)

FOREIGN PATENT DOCUMENTS

| | | |
|---|---|---|
| WO | WO 96/12448 A1 | 5/1996 |
| WO | WO 00/56245 A2 | 9/2000 |

(Continued)

OTHER PUBLICATIONS

International Search Report and Written Opinion.

*Primary Examiner* — Todd J Scherbel
*Assistant Examiner* — Son Dang
(74) *Attorney, Agent, or Firm* — Brinks Gilson & Lione

(57) ABSTRACT

A removable vena cava filter configured for reduced trauma and enhanced visualization of anchoring hook placement relative to the vessel wall is disclosed. The filter includes a plurality of struts, each having an anchoring hook and a stop member proximate the anchoring hook. The stop members are configured to engage the vessel wall to prevent excessive penetration of the anchoring hooks into the vessel wall and to aid in the identification of anchoring hook placement relative to the vessel wall.

8 Claims, 7 Drawing Sheets

Related U.S. Application Data

(60) Provisional application No. 61/294,269, filed on Jan. 12, 2010.

(51) Int. Cl.
*A61F 2/01* (2006.01)
*A61F 2/30* (2006.01)

(52) U.S. Cl.
CPC . *A61F 2230/008* (2013.01); *A61F 2250/0026* (2013.01); *A61F 2250/0098* (2013.01)

(56) References Cited

U.S. PATENT DOCUMENTS

| | | | |
|---|---|---|---|
| 5,242,462 | A | 9/1993 | El-Nounou et al. |
| 6,007,558 | A | 12/1999 | Ravenscroft et al. |
| 6,217,600 | B1 | 4/2001 | DiMatteo |
| 6,517,559 | B1 | 2/2003 | O'Connell |
| 6,540,767 | B1 | 4/2003 | Walak et al. |
| 7,704,267 | B2 | 4/2010 | Tessmer |
| 7,976,562 | B2 | 7/2011 | Bressler et al. |
| 8,500,774 | B2 | 8/2013 | McGuckin, Jr. et al. |
| 8,795,351 | B2 | 8/2014 | Weidman |
| 2001/0039431 | A1 | 11/2001 | DeVries et al. |
| 2004/0158273 | A1 | 8/2004 | Weaver et al. |
| 2004/0158274 | A1* | 8/2004 | WasDyke .............. A61F 2/01 606/200 |
| 2004/0186510 | A1 | 9/2004 | Weaver |
| 2004/0230220 | A1 | 11/2004 | Osborne |
| 2005/0055045 | A1 | 3/2005 | Devries et al. |
| 2005/0107822 | A1 | 5/2005 | Wasdyke |
| 2005/0159771 | A1* | 7/2005 | Petersen .............. A61F 2/01 606/200 |
| 2005/0234503 | A1 | 10/2005 | Ravenscroft et al. |
| 2005/0251199 | A1 | 11/2005 | Osborne et al. |
| 2005/0267512 | A1 | 12/2005 | Osborne et al. |
| 2005/0267513 | A1 | 12/2005 | Osborne et al. |
| 2005/0267514 | A1 | 12/2005 | Osborne et al. |
| 2005/0288704 | A1 | 12/2005 | Cartier et al. |
| 2006/0015137 | A1 | 1/2006 | WasDyke et al. |
| 2006/0069405 | A1 | 3/2006 | Schaeffer et al. |
| 2006/0069406 | A1 | 3/2006 | Hendriksen et al. |
| 2006/0095068 | A1 | 5/2006 | WasDyke et al. |
| 2006/0100660 | A1 | 5/2006 | Osborne et al. |
| 2007/0005095 | A1 | 1/2007 | Osborne et al. |
| 2007/0112373 | A1* | 5/2007 | Carr, Jr. .............. A61F 2/01 606/200 |
| 2007/0167974 | A1 | 7/2007 | Cully et al. |
| 2008/0221609 | A1 | 9/2008 | McGuckin et al. |
| 2010/0121373 | A1 | 5/2010 | Tekulve |
| 2010/0318115 | A1 | 12/2010 | Chanduszko et al. |
| 2011/0202086 | A1 | 8/2011 | Bates |

FOREIGN PATENT DOCUMENTS

| | | |
|---|---|---|
| WO | WO 03/075793 A1 | 9/2003 |
| WO | WO 2006/034233 A1 | 3/2006 |
| WO | WO 2011/014703 A1 | 2/2011 |

* cited by examiner

VISUAL STABILIZER ON ANCHOR LEGS OF VENA CAVA FILTER

CROSS-REFERENCE TO RELATED APPLICATIONS

This application is a continuation of U.S. application Ser. No. 13/521,458, filed Jan. 12, 2011 related to and claims the benefit of priority to PCT/US2011/020950, filed Jan. 12, 2011, which application claims the benefit of U.S. Provisional Application No. 61/294,269, filed on Jan. 12, 2010, entitled "Visual Stabilizer on Anchor Legs of Vena Cava Filter," all of which the entire contents of which are incorporated herein by reference.

BACKGROUND OF THE INVENTION

Field of Invention

The present invention relates to medical devices. More particularly, the invention relates to a removable vena cava filter that can be percutaneously placed in and removed from the vena cava of a patient with reduced trauma and enhanced visualization of anchoring hook placement relative to the vena cava wall.

Background

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the venous peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

The benefits of a vena cava filter have been well established, but improvements may be made. For example, filters generally have some type of anchoring member to anchor the filter to the vena cava wall. With such anchoring members, there is a risk of increased trauma to the vena cava wall should the filter be inadvertently and/or improperly moved, thus causing further penetration of the anchoring member into or through the vena cava wall.

BRIEF SUMMARY OF THE INVENTION

The present invention generally provides a removable vena cava filter for capturing thrombi in a blood vessel. In one embodiment, the filter includes a plurality of struts having a collapsed state for filter retrieval or delivery and an expanded state for engaging with a vessel wall of the blood vessel. The struts have first ends attached together along a longitudinal axis of the filter. The struts extend from the first ends to second ends. Each strut includes a proximal portion extending from the first end and a distal portion extending from the proximal portion to the second end. The distal portion of each strut includes an anchoring hook configured to penetrate the vessel wall and a stop member proximate the anchoring hook. The stop member is configured to engage the vessel wall to prevent further penetration of the anchoring hook into or through the vessel wall and to reduce trauma to the vessel wall. In addition, the stop member enhances visualization of the anchoring hook and its position relative to the vessel wall.

In another embodiment, the removable filter includes a plurality of struts having a collapsed state for filter retrieval or delivery and an expanded state for engaging with a vessel wall of the blood vessel. Each strut extends from a first end to a second end. The first ends of the struts are attached together along a longitudinal axis of the filter. Each strut extends arcuately along the longitudinal axis and includes a proximal portion extending from the first end and a distal portion extending from the proximal portion to the second end. The distal portion of each strut includes an anchoring hook configured to penetrate the vessel wall and a stop member configured to engage the vessel wall to prevent further penetration of the anchoring hook into or through the vessel wall. The stop member is further configured to enhance visualization of the anchoring hook and its position relative to the vessel wall. The stop member is formed separately from the strut and attached to the strut adjacent the anchoring hook such that the stop member extends distally from the anchoring hook. The second end of each strut thus terminates with the stop member.

In yet another embodiment, the removable filter includes a central axis and a plurality of struts having a collapsed state for filter retrieval or delivery and an expanded state for engaging with a vessel wall of a blood vessel. Each strut extends from a first end to a second end and terminates with an anchoring hook at the second end. The first ends are attached together along the central axis. The anchoring hooks are configured to penetrate the vessel wall to anchor the filter to the vessel wall. Each strut includes a stop member disposed proximally relative to the anchoring hook. The stop members are configured to engage the vessel wall to prevent further penetration of the anchoring hooks into and through the vessel wall and to reduce trauma to the vessel wall. The stop members are formed of a radiopaque material to enhance visualization of the anchoring hooks and their respective positions relative to the vessel wall.

Further aspects, features, and advantages of the invention will become apparent from consideration of the following description and the appended claims when taken in connection with the accompanying drawings.

DETAILED DESCRIPTION OF THE INVENTION

The following provides a detailed description of currently preferred embodiments of the present invention. The description is not intended to limit the invention in any manner, but rather serves to enable those skilled in the art to make and use the invention.

Figures 1, 1A:
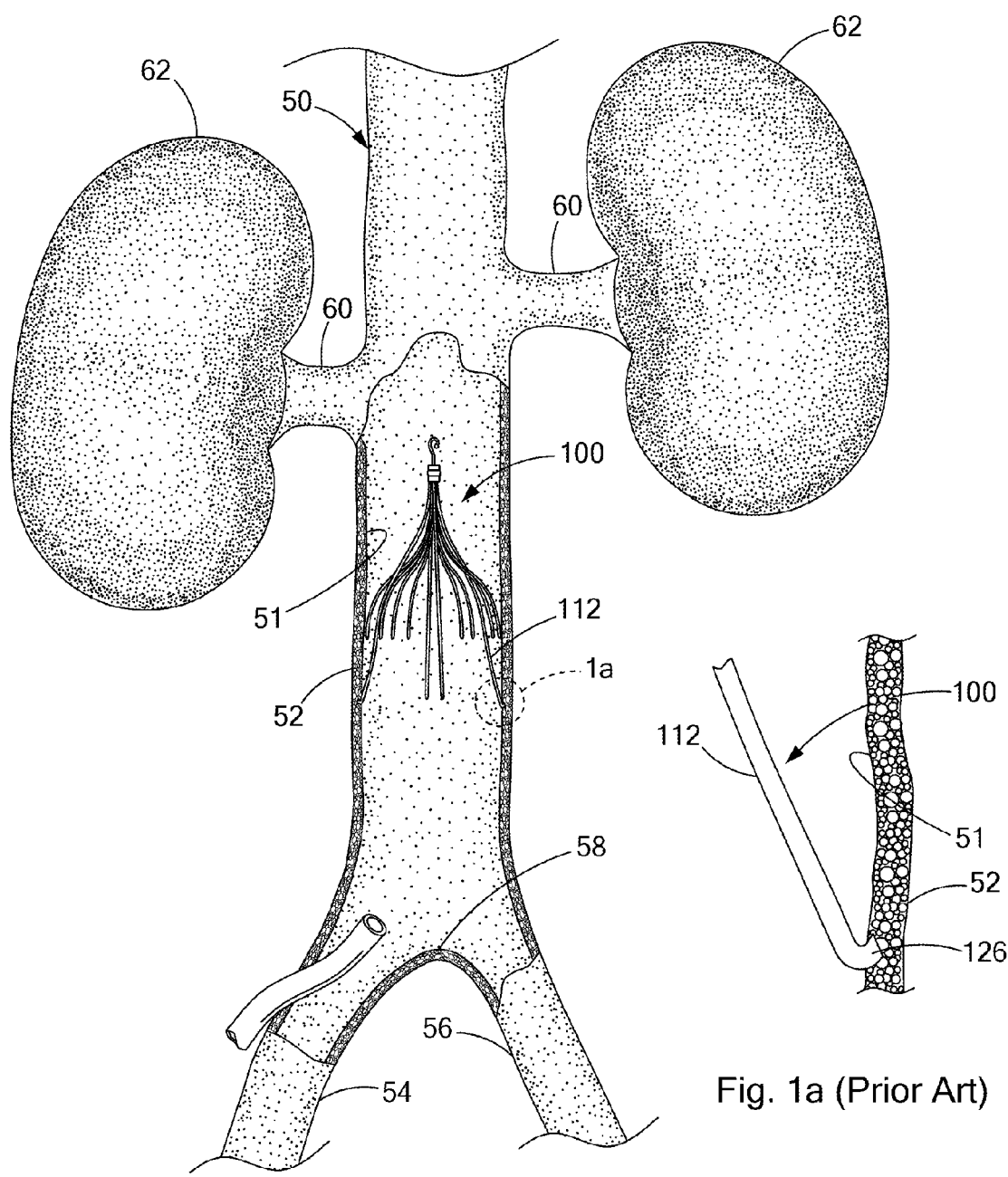
FIG. 1 is an illustration of the anatomy of the renal veins, the iliac veins, and the vena cava in which a prior art filter has been deployed.
FIG. 1a is an enlarged view of the prior art filter in circle 1a of FIG. 1, depicting an anchoring hook engaged in the vessel wall.

Referring now to FIG. 1, a vena cava filter found in the prior art, denoted by reference numeral 100, is implanted in the vena cava 50 for the purpose of lysing or capturing thrombi carried by the blood flowing through the iliac veins 54, 56 toward the heart and into the pulmonary arteries. As shown, the iliac veins 54, 56 merge at juncture 58 into the vena cava 50. The renal veins 60 from the kidneys 62 join the vena cava 50 downstream of juncture 58. The portion of the vena cava 50 between the juncture 58 and the renal veins 60 defines the inferior vena cava 52 in which the vena cava filter 100 has been percutaneously deployed through one of the femoral veins or one of the jugular veins.

As depicted in FIG. 1, the prior art filter 100 includes a plurality of primary struts 112 which terminate with an anchoring hook 126 for anchoring the filter 100 in the vena cava wall 51. FIG. 1a shows an anchoring hook 126 piercing the vena cava wall 51. As the anchoring hook 126 anchors to the vena cava wall 51, the anchoring hook 126 makes a small cut or pokes a small hole in the vena cava wall 51. Movement of the filter 100 can cause the anchoring hook 126 to penetrate further into and through the vena cava wall 51 via the small cut or hole, causing increased trauma to the vena cava wall 51.

Embodiments of the present invention provide an improved filter having stop members configured to prevent excessive penetration of the anchoring hooks into and through the vena cava wall. Moreover, the stop members of the improved filter aid in visualization of filter placement and, specifically, identification of placement of the anchoring hooks relative to the vena cava wall.

Figure 2:
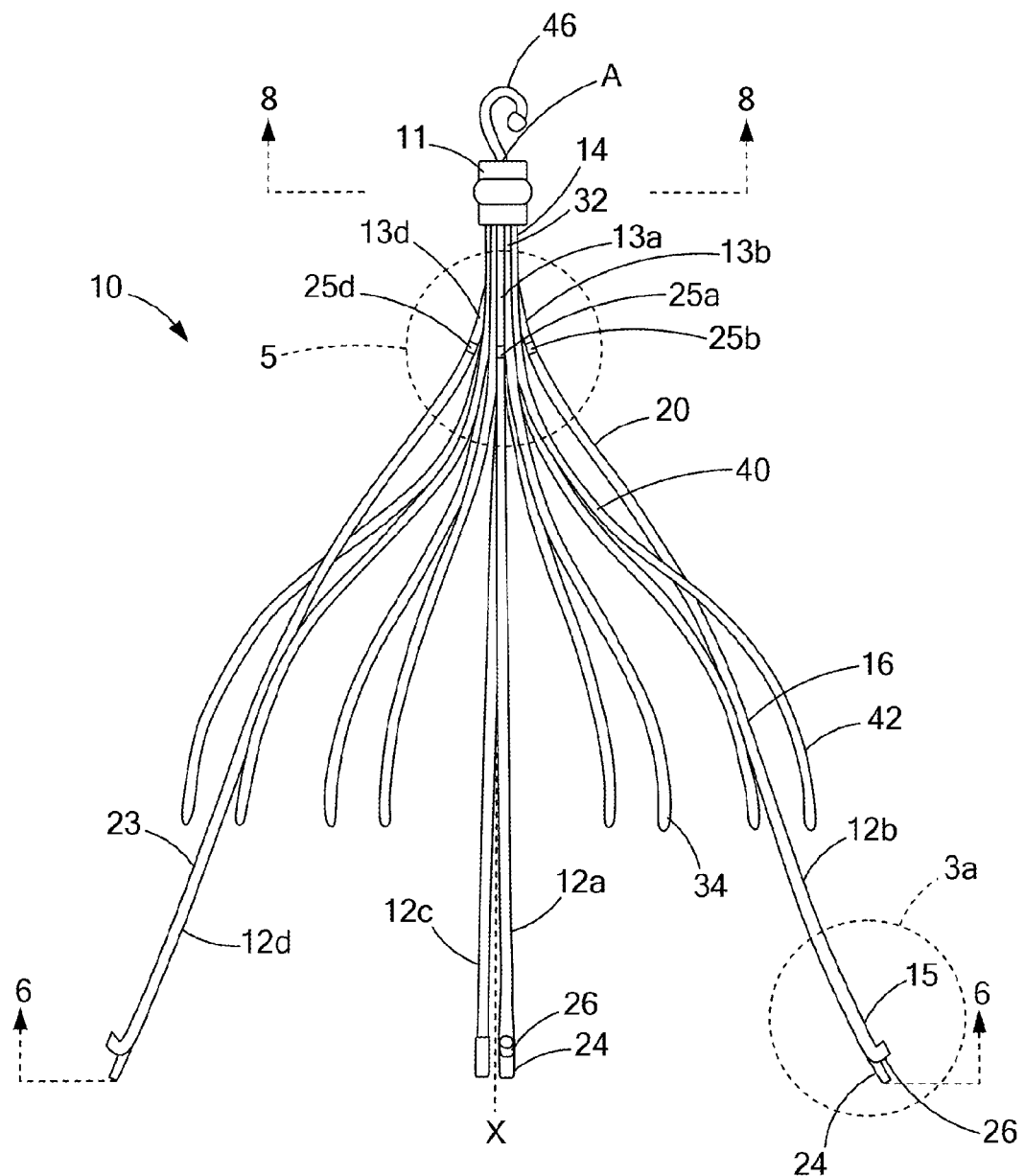
FIG. 2 is a side perspective view of one embodiment of a vena cava filter of the present invention, shown in an expanded state.

FIG. 2 illustrates a vena cava filter 10 in accordance with a preferred embodiment of the present invention. As shown in FIG. 2, the filter 10 is in an expanded state and comprises four filter legs or primary struts 12a-d, each having first ends 14 that emanate from a hub 11. The hub 11 attaches by crimping the first ends 14 of the primary struts 12a-d together along a center point A in a compact bundle along a central or longitudinal axis X of the filter. The hub 11 has a minimal diameter for the size of wire used to form the primary struts 12a-d.

Preferably, the primary struts 12a-d are formed from a spring material or a superelastic material, including but not limited to stainless steel, cobalt-chromium-nickel-molybdenum-iron alloy, cobalt-chrome alloy, nitinol, or any other suitable material that will result in a self-opening or self-expanding filter. In this embodiment, the primary struts 12a-d are preferably formed from wire having a round or near round cross-section with a diameter of at least about 0.015 inches. Of course, it is not necessary that the primary struts have a round cross-section. For example, the primary struts 12a-d could take on any shape with rounded edges to maintain non-turbulent blood flow therethrough.

As shown in FIG. 2, each primary strut 12a-d extends from the first end 14 to a second end 15 and includes an arcuate segment 16 having a soft S-shape. Each arcuate segment 16 is formed with a first curved proximal portion 20 that is configured to softly bend away from the longitudinal axis X of the filter 10 and a second curved distal portion 23 that is configured to softly bend toward the longitudinal axis of the filter 10. Due to the soft bends of each arcuate segment 16, a prominence or a point of inflection on the primary strut 12a-d is substantially avoided to aid in non-traumatically engaging the vena cava or vessel wall 51. As explained in more detail below with reference to FIGS. 5 and 6, the first curved proximal portion 20 of each primary strut 12a-d has an axial or circumferential bend 25a-d.

Figure 6:
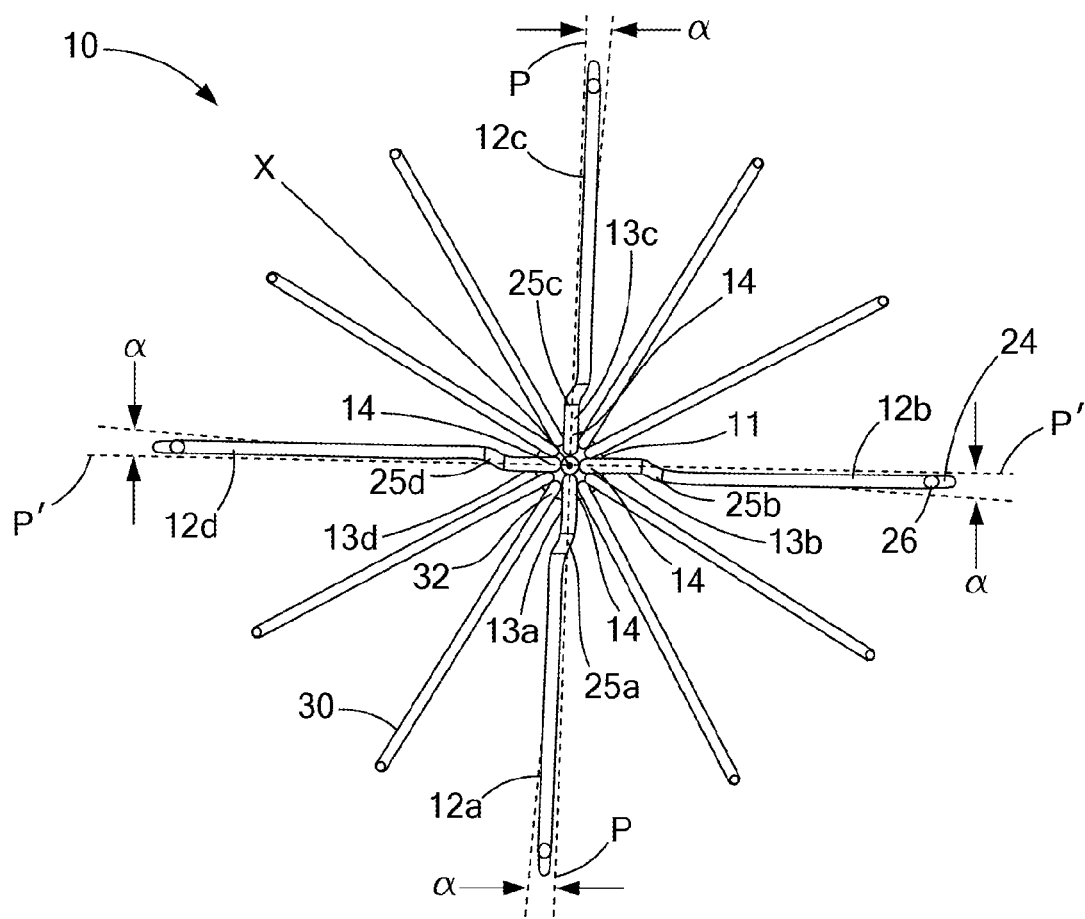
FIG. 6 is an end view of the filter in FIG. 2 taken along line 6-6.

As illustrated in FIG. 2, each of the primary struts 12a-d is an anchor leg, including an anchoring hook 26 at the second end 15 that will anchor in the vessel wall 51 when the filter 10 is deployed at a delivery location in the blood vessel. The primary struts 12a-d are configured to move between the expanded state for engaging the anchoring hooks 26 with the blood vessel and the collapsed state for filter retrieval or delivery. In the expanded state, each arcuate segment 16 extends arcuately along a longitudinal X (as shown in FIG. 2) and substantially linearly along a diametric plane (as shown in FIG. 6) to avoid entanglement with other primary struts 12a-d.

As discussed in greater detail below, the soft bends of each arcuate segment 16 allow each primary strut 12a-d to cross another primary strut 12a-d along the longitudinal axis X in the collapsed state such that each anchoring hook 26 faces the longitudinal axis X for filter retrieval or delivery.

When the filter 10 is deployed in a blood vessel 52, the anchoring hooks 26 at the second ends 15 of the primary struts 12a-d engage the inner wall 51 of the blood vessel 52 to define a first axial portion to secure the filter 10 in the blood vessel 52. The anchoring hooks 26 prevent the filter 10 from migrating from the delivery location in the blood vessel 52 where it has been deposited. The primary struts 12a-d are shaped and dimensioned such that, when the filter 10 is freely expanded, the filter 10 has a diameter of between about 25 mm and 45 mm and a length of between about 3 cm and 7 cm. For example, the filter 10 may have a diameter of about 35 mm and a length of about 5 cm. The primary struts 12a-d have sufficient spring strength that when the filter 10 is deployed the anchoring hooks 26 will anchor into the vessel wall 51.

Figure 3A:
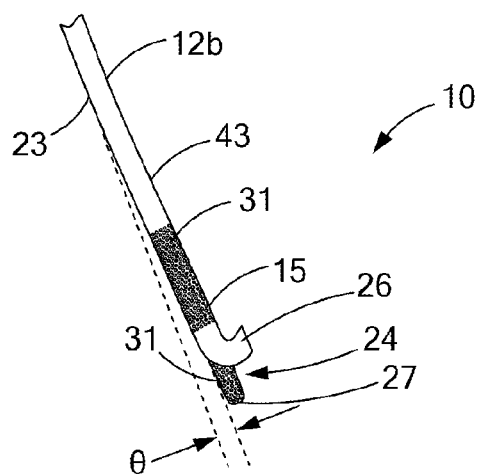
FIG. 3a is an enlarged view of circle 3a in FIG. 2.
Figure 4A:
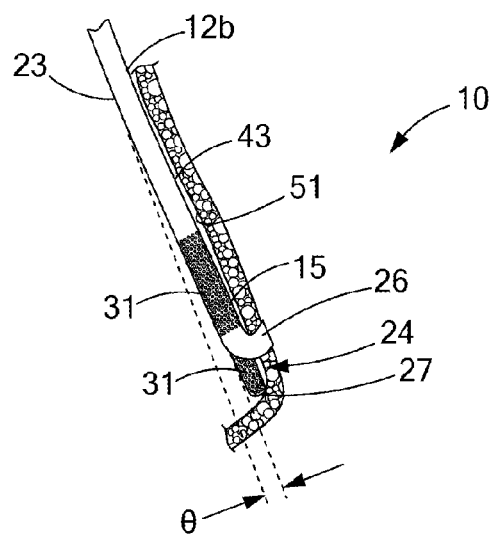
FIGS. 4a-e show the anchoring hooks of the filter legs of FIGS. 3a-e, respectively, penetrating a vessel wall.

Referring to FIGS. 3a and 4a, the second curved distal portion 23 of each of the primary struts 12a-d includes a stabilizer, or stop member, 24 in close proximity to the anchoring hook 26. As provided above, the anchoring hooks 26 prevent migration of the filter 10 within the blood vessel. The anchoring hooks 26 accomplish this by piercing a small hole, or making a small cut, in the vessel wall 51 to penetrate the vessel wall 51. The stop members 24 are configured to prevent further, excessive penetration of the anchoring hook 26 through the hole or cut in the vessel wall 51. In addition, the stop members 24 provide enhanced visualization of the anchoring hooks 26 and their respective positions relative to the vessel wall 51.

In this embodiment, each stop member 24 is disposed distally relative to the anchoring hook 26 such that the second end 15 of each primary strut 12a-d terminates with the stop member 24. Each stop member 24 is formed separately from each primary strut 12a-d and is attached to the second end 15 of each primary strut 12a-d at the curved portion of the anchoring hook 26. Preferably, the stop member 24 is welded to each primary strut 12a-d, although the stop member 24 may be attached to the primary strut 12a-d by any other suitable attachment means, including but not limited to soldering or gluing. In this embodiment, the length of the stop member 24 (i.e., the distance the stop member 24 extends from the anchoring hook 26) is between about 0.5 mm and about 10.0 mm. The diameter of the stop member 24 is preferably about the same diameter of the primary strut 12a-d, give or take about 0.2 mm. In this embodiment, the distal tip 27 of the stop member 24 is rounded so that it is atraumatic to the vessel wall 51.

As illustrated in FIG. 4a, in the event external compression of the vessel 52, or movement of the filter 10, causes the anchoring hooks 26 to move toward further penetration into the vessel wall 51, the stop members 24 are configured to engage or abut the vessel wall 51 to prevent further penetration of the anchoring hooks 26. In this embodiment, the stop member 24 is atraumatic and thus does not pierce the vessel wall 51. Rather, as shown in FIG. 4a, the stop member 24 pushes against the vessel wall 51, thereby preventing the anchoring hook 26 from further penetrating into the vessel wall 51. Accordingly, each stop member 24 is configured to reduce the likelihood of increased trauma to the vessel wall 51 caused by further penetration of the adjacent anchoring hook 26 into or through the vessel wall 51.

Additionally, the stop members 24 provide physicians with the ability to identify placement of the anchoring hooks 26 relative to the vena cava wall 51. The stop members 24 are thus preferably formed from a different material than the primary struts 12a-d, most preferably a radiopaque material, such as platinum, palladium or any suitable radiopaque material known in the art.

Moreover, the stop members 24 preferably include a plurality of dimples 31 formed on an outer surface thereof to further enhance visualization of anchoring hook 26 placement, not only under x-ray examination, but under ultrasound examination as well. The dimples 31 provide the outer surface of the stop members 24 with the desired surface irregularities capable of reflecting ultrasound waves. In a preferred embodiment, the dimples 31 are small, circular indentations impressed upon the outer surface of the stop members 24 by any suitable means known in the art and have a diameter of approximately 0.1 mm and a depth of approximately 0.01 mm. They are preferably distributed over the entire outer surface of the stop members 24. The dimples 31 may be formed on the stop members 24 before or after attachment thereof to the primary struts 12. It is also within the scope of the present invention for a plurality of dimples 31 to be formed on a portion of the outer surface of the primary struts 12 adjacent the anchoring hook 26, as shown in FIGS. 3a and 4a, to further enhance visualization of the filter 10 via ultrasound.

Figure 3B:
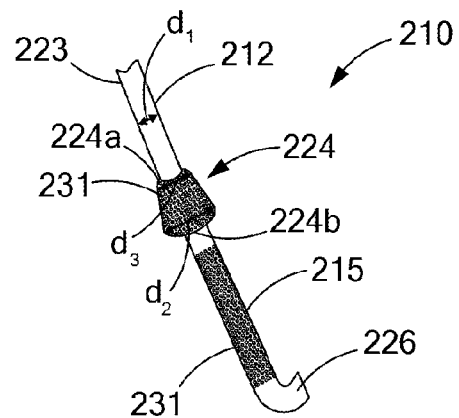
FIGS. 3b-e are enlarged views of a filter leg in accordance with alternative embodiments of the present invention.
Figure 4B:
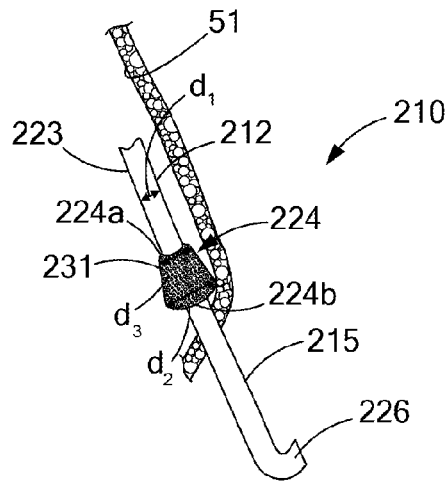

FIGS. 3b and 4b depict an alternative embodiment of a primary strut 212 of a filter 210 in accordance with the teachings of the present invention and having a description similar to that of FIGS. 3a and 4a, and in which similar components are denoted by similar reference numerals increased by 200. In this embodiment, the stop member 224 is disposed proximally relative to the anchoring hook 226 such that the second end 215 terminates with the anchoring hook 226. The stop member 224 projects radially outward from the primary strut 212 to provide a portion of the primary strut 212 having an increased circumferential area.

As shown in FIGS. 3b and 4b, the stop member 224 is a conical annular band having an apex region 224a and a base 224b. The stop member 224 has an inner diameter sized and configured to receive the primary strut 212. In this embodiment, the primary strut 212 has an outer diameter $d_1$, the base 224b of the stop member 224 has an outer diameter $d_2$ greater than the outer diameter $d_1$ of the primary strut 212, and the apex region 224a of the stop member 224 has an outer diameter $d_3$ smaller than the outer diameter $d_2$ of the base 224b and slightly larger than outer diameter $d_1$ of the primary strut 212. As illustrated in FIG. 3b, the outer diameter of the conical annular stop member 224 tapers proximally from the base 224b to the apex region 224a.

As previously stated, the stop member 224 provides a portion of each primary strut 212 with an increased circumferential area. As depicted in FIGS. 3b and 4b, the anchoring hook 226 is curved in a direction toward the hub and the stop member 224 extends in a direction away from the hub, i.e., the stop member 224 radially expands from the apex region 224a to the base 224b. In this embodiment, each stop member 224 is formed separately from the primary strut 212 and is attached to the distal portion 223 of each primary strut 212 proximally relative to the anchoring hook 226. In one example, the annular stop member 224 may be slid over the second end 215 of the primary strut 212 prior to forming the anchoring hook 226 at the terminal end of the primary strut 212. Once in a desired position, the stop member 224 may be attached to the primary strut 212 by any suitable means known in the art, including but not limited to crimping, soldering, gluing, or laser welding. Thereafter, the anchoring hook 226 may be formed by curving the terminal end of the primary strut 212 in a direction toward the hub. Preferably, the stop member 224 is disposed between about 2 mm and about 10 mm, and most preferably about 5 mm, from the anchoring hook 226.

As illustrated in FIG. 4b, in the event external compression of the vessel 52, or movement of the filter 210, causes the anchoring hooks 226 to move toward further penetration into the vessel wall 51, the opposite orientation of the anchoring hook 226 and corresponding stop member 224 of each primary strut 212 is configured to prevent further penetration of the anchoring hooks 226 into the vessel wall 51. Moreover, the increased circumferential area of the primary strut 212, i.e., the stop member 224, is configured to engage or abut the vessel wall 51 to prevent further penetration of the anchoring hooks 226. Preferably, as shown in FIG. 4b, the base 224b of the stop member 224 pushes against the vessel wall 51, thereby preventing the anchoring hook 226 from further penetrating into the vessel wall 51. Accordingly, the stop member 224 is configured to reduce the likelihood of increased trauma to the vessel wall 51 caused by further penetration of the anchoring hook 226 into the vessel wall 51.

Figure 3C:
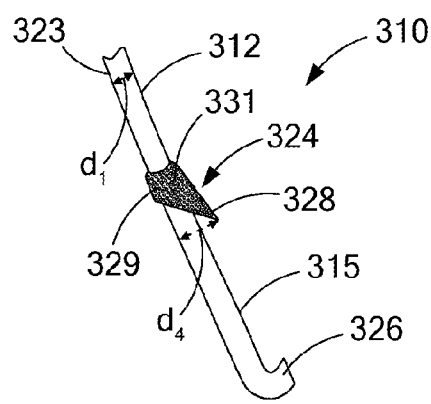
Figure 4C:
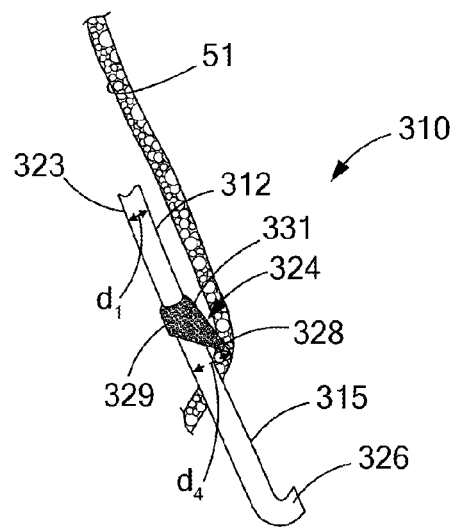

FIGS. 3c and 4c depict an alternative embodiment of a primary strut 312 of a filter 310 in accordance with the teachings of the present invention and having a description similar to that of FIGS. 3a and 4a, and in which similar components are denoted by similar reference numerals increased by 300. In this embodiment, the stop member 324 is disposed proximally relative to the anchoring hook 326 such that the second end 315 terminates with the anchoring hook 326. The stop member 324 projects radially outward from the primary strut 312 to provide a portion of the primary strut 312 with an increased circumferential area. As shown in FIGS. 3c and 4c, the stop member 324 is an annular band having a cylindrical ring portion 329 and a barb extension 328 formed unitarily therewith. The stop member 324 has an inner diameter sized and configured to receive the primary strut 312 and the barb extension 328 extends radially from the primary strut 312 in a direction away from the longitudinal axis X when the filter 310 is in the expanded state. In this embodiment, the primary strut 312 has an outer diameter $d_1$ and the barb extension 328 extending radially from the primary strut 312 defines an outer diameter $d_4$ greater than the outer diameter $d_1$.

As provided above, the stop member 324 includes a barb extension 328, which defines an increased outer diameter $d_4$, and thus provides a portion of each primary strut 312 with an increased circumferential area. As shown in FIGS. 3c and 4c, the anchoring hook 326 is curved in a direction toward the hub and the barb extension 328 extends in a direction away from the hub. In this embodiment, each stop member 324 is preferably formed separately from the primary strut 312 and is attached to the distal portion 323 of each primary strut 312 proximally relative to the anchoring hook 326. In one example, the annular stop member 324 may be slid over the second end 315 of the primary strut 312 prior to forming the anchoring hook 326 at the terminal end of the primary strut 312. Once in a desired position, the stop member 324 may be attached to the primary strut 312 by any suitable means known in the art, including but not limited to crimping, soldering, gluing, or laser welding. Thereafter, the anchoring hook 326 may be formed by curving the terminal end of the primary strut 312 in a direction toward the hub. Preferably, the stop member 324 is disposed between about 2 mm and about 10 mm, and most preferably about 5 mm, from the anchoring hook 326.

As illustrated in FIG. 4c, in the event external compression of the vessel 52, or movement of the filter 310, causes the anchoring hooks 326 to move toward further penetration into the vessel wall 51, the opposite orientation of the anchoring hook 326 and corresponding barb extension 328 of each primary strut 312 is configured to prevent further penetration of the anchoring hooks 326 into the vessel wall. Moreover, the increased circumferential area of the primary strut 312, i.e., the stop member 324, is configured to engage or abut the vessel wall 51 to prevent further penetration of the anchoring hooks 326. Preferably, as shown in FIG. 4c, the barb extension 328 of the stop member 324 pushes against the vessel wall 51, thereby preventing the anchoring hook 326 from further penetrating into the vessel wall 51. Accordingly, the stop member 324 is configured to reduce the likelihood of increased trauma to the vessel wall 51 caused by further penetration of the anchoring hook 326 into the vessel wall 51.

In this embodiment, the barb extension 328 preferably has a sharpened tip which engages or anchors into the vessel wall 51 to prevent further penetration of the anchoring hook 326. Preferably, the sharpened tip functions as an additional hooking member. As opposed to a round-shaped stop member, the sharpened tip of the barb extension 328 is able to pierce the wall, thus providing a higher resistance against the vessel wall 51 to prevent the strut 312 from penetrating further.

Figure 3D:
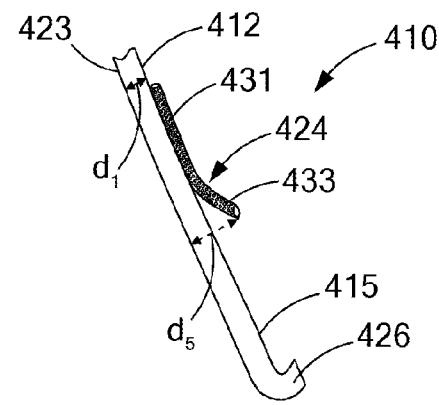
Figure 4D:
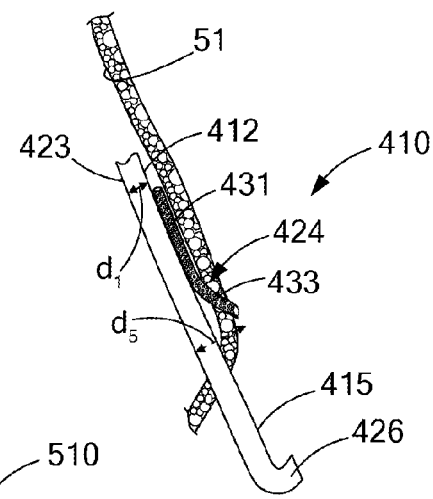

FIGS. 3d and 4d depict an alternative embodiment of a primary strut 412 of a filter 410 in accordance with the teachings of the present invention and having a description similar to that of FIGS. 3a and 4a, and in which similar components are denoted by similar reference numerals increased by 400. In this embodiment, the stop member 424 is disposed proximally relative to the anchoring hook 426 such that the second end 415 terminates with the anchoring hook 426. The stop member 424 projects radially outward from the primary strut 412 to provide a portion of the primary strut 412 with an increased circumferential area. As shown in FIGS. 3d and 4d, the stop member 424 is a bent or curved wire filament having a tangential portion 431 tangential to and attached to the primary strut 412 and a projecting portion 433 projecting radially outward from the primary strut 412, i.e., in a direction away from the longitudinal axis X, when the filter 410 is in the expanded state.

In this embodiment, the primary strut 412 has an outer diameter $d_1$ and the projecting portion 433 of the stop member 424 extending radially from the primary strut 412 defines an outer diameter $d_5$ greater than the outer diameter $d_1$. Preferably, the projecting portion 433 is bent at an angle of about 45 degrees with respect to an axis defined by the distal portion 423 of the primary strut 412, as illustrated in FIG. 3d. The difference between $d_5$ and $d_1$ is preferably about 1 mm, i.e., the projecting portion 433 projects about 1 mm from the primary strut 412.

As previously stated, the stop member 424 defines an increased outer diameter $d_5$, and thus provides a portion of each primary strut 412 with an increased circumferential area. As shown in FIGS. 3d and 4d, the anchoring hook 426 is curved in a direction toward the hub and the projecting portion 433 of the stop member 424 extends in a direction away from the hub. In this embodiment, each stop member 424 is formed separately from the primary strut 412 and is attached to the distal portion 423 of each primary strut 412 proximally relative to the anchoring hook 426. In one example, the tangential portion 431 of the stop member 424 is attached to the primary strut 412 by any suitable means known in the art, including but not limited to crimping, soldering, gluing, or laser welding. Preferably, the stop member 424 is disposed between about 2 mm and about 10 mm, and most preferably about 5 mm, from the anchoring hook 426.

As illustrated in FIG. 4d, in the event external compression of the vessel 52, or movement of the filter 410, causes the anchoring hooks 426 to move toward further penetration into the vessel wall 51, the opposite orientation of the anchoring hook 426 and corresponding projecting portion 433 of the stop member 424 of each primary strut 412 is configured to prevent further penetration of the anchoring hooks 426 into the vessel wall. Moreover, the increased circumferential area of the primary strut 412, i.e., the stop member 424, is configured to engage or abut the vessel wall 51 to prevent further penetration of the anchoring hooks 426. Preferably, as shown in FIG. 4d, the projecting portion 433 of the stop member 424 pushes against the vessel wall 51, thereby preventing the anchoring hook 426 from further penetrating into the vessel wall 51. Accordingly, the stop member 424 is configured to reduce the likelihood of increased trauma to the vessel wall 51 caused by further penetration of the anchoring hook 426 into the vessel wall 51.

In this embodiment, the projecting portion 433 may have a sharpened tip which engages or anchors into the vessel wall 51 to prevent further penetration of the anchoring hook 426. Preferably, the sharpened tip functions as an additional hooking member. As opposed to a round-shaped stop member, the sharpened tip of the projecting portion 433 is able to pierce the wall, thus providing a higher resistance against the vessel wall 51 to prevent the strut 412 from penetrating further.

Figure 3E:
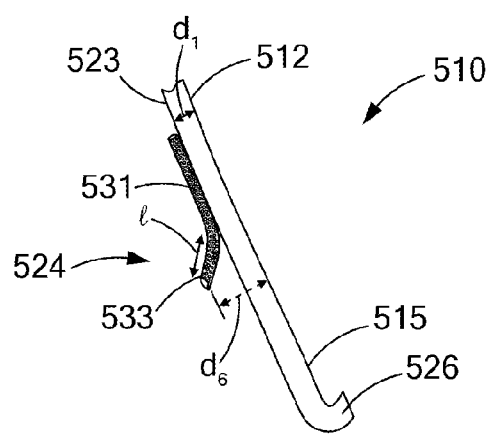
Figure 4E:
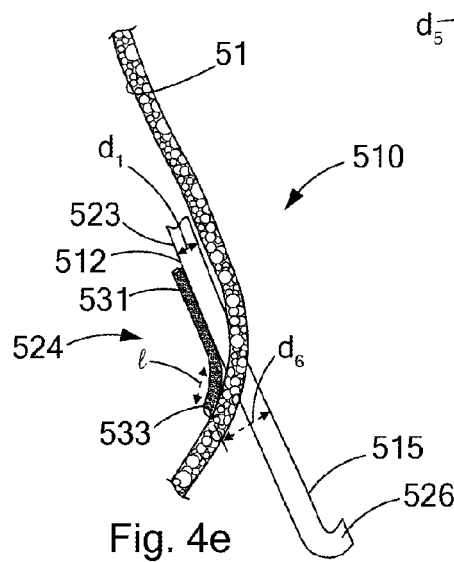

FIGS. 3e and 4e depict an alternative embodiment of a primary strut 512 of a filter 510 in accordance with the teachings of the present invention and having a description similar to that of FIGS. 3a and 4a, and in which similar components are denoted by similar reference numerals increased by 500. In this embodiment, the stop member 524 is disposed proximally relative to the anchoring hook 526 such that the second end 515 terminates with the anchoring hook 526. The stop member 524 projects radially inward from the primary strut 512, as opposed to projecting radially outward in the embodiment of FIGS. 3d and 4d, to provide a portion of the primary strut 512 with an increased circumferential area. As shown in FIGS. 3e and 4e, the stop member 524 is a bent or curved wire filament having a tangential portion 531 tangential to and attached to the primary strut 512 and a projecting portion 533 projecting radially inward from the primary strut 412, i.e., in a direction toward the longitudinal axis X, when the filter 510 is in the expanded state.

In this embodiment, the primary strut 512 has an outer diameter $d_1$ and the projecting portion 533 of the stop member 524 extending radially from the primary strut 512 defines an outer diameter $d_6$ greater than the outer diameter $d_1$. Preferably, the projecting portion 533 is bent at an angle of about 45 degrees with respect to an axis defined by the distal portion 523 of the primary strut 512, as illustrated in FIG. 3e. The difference between $d_6$ and $d_1$ is preferably about 1 mm, i.e., the projecting portion 533 projects about 1 mm from the primary strut 512.

As previously stated, the stop member 524 defines an increased outer diameter $d_6$, and thus provides a portion of each primary strut 512 with an increased circumferential area. As shown in FIGS. 3e and 4e, the anchoring hook 526 is curved in a direction toward the hub and the projecting portion 533 of the stop member 524 extends in a direction away from the hub. In this embodiment, each stop member 524 is formed separately from the primary strut 512 and is attached to the distal portion 523 of each primary strut 512 proximally relative to the anchoring hook 526. In one example, the tangential portion 531 of the stop member 524 is attached to the primary strut 512 by any suitable means known in the art, including but not limited to crimping, soldering, gluing, or laser welding. Preferably, the stop member 524 is disposed between about 2 mm and about 10 mm, and most preferably about 5 mm, from the anchoring hook 526.

As illustrated in FIG. 4e, in the event external compression of the vessel 52, or movement of the filter 510, causes the anchoring hooks 526 to move toward further penetration into the vessel wall 51, the opposite orientation of the anchoring hook 526 and corresponding projecting portion 533 of the stop member 524 of each primary strut 512 is configured to prevent further penetration of the anchoring hooks 526 into the vessel wall. Moreover, the increased circumferential area of the primary strut 512, i.e., the stop member 524, is configured to engage or abut the vessel wall 51 to prevent further penetration of the anchoring hooks 526.

Preferably, as shown in FIG. 4e, the backside of the projecting portion 533 of the stop member 524, rather than the tip of the projecting portion 433 of the stop member 424 in FIG. 4d, pushes against the vessel wall 51, thereby preventing the anchoring hook 526 from further penetrating into the vessel wall 51. As shown in FIG. 4e, the backside of the projecting portion 533 is substantially tangent to the vessel wall 51, i.e., substantially the entire length l of the projecting portion 533 abuts the vessel wall 51, providing a larger contact area configured to engage the vessel wall 51, and thus a higher resistance to prevent further penetration by the anchoring hooks 526. Accordingly, the stop member 524 is configured to reduce the likelihood of increased trauma to the vessel wall 51 caused by further penetration of the anchoring hook 526 into the vessel wall 51.

While the stop members of FIGS. 3a-e are preferably a radiopaque material and formed separately from respective primary struts, the stop members 424, 524 in FIGS. 3d and 3e may be formed integrally, i.e., unitarily, with respective primary struts 412, 512 by laser cutting a series of slits in the primary struts 412, 512 and bending the portion of the primary struts 412, 512 defined by the slits to resemble the projecting portion 433, 533 of the separate wire filament stop member 424, 524 discussed above.

It is noted that the anchoring hooks and stop members shown and described with respect to FIGS. 3a-e may be incorporated with alternative filter designs, including but not limited to the filter described in U.S. Pat. No. 5,133,733 to Rasmussen et al., the entire contents of which are incorporated herein by reference.

As shown in FIG. 3a, each primary strut 12a-d preferably includes a distal bend 43 formed thereon and extending outwardly radially from the longitudinal axis X. In this embodiment, the distal bend 43 may extend outwardly at an angle θ between about 0.5 degree and 2 degrees, preferably 1 degree. The distal bend 43 may be situated at a distance from the anchoring hook 26, which is arranged at the end of a substantially straight strut segment. The distal bend 43 may have a length of between about 1 and 7 mm, preferably between about 2 and 4 mm. The distal bend 43 allows the filter 10 to filter thrombi effectively at a smaller inside diameter of a blood vessel than otherwise would be possible while maintaining the ability to collapse for delivery or retrieval. Further, the distal bend 43 provides for a more firm engagement of the anchoring hook 26 at the vessel wall. At the engagement of the anchoring hook 26 with the vessel wall, the primary struts 12a-d will urge the vessel wall outwards, whereas the vessel wall will urge the primary struts 12a-d inwards toward the longitudinal axis X of the filter 10. It is noted that any of the alternative embodiments illustrated in FIGS. 3b-d may also include such a distal bend. In a preferred embodiment, the anchoring hooks 26 are angled by between about 50 and 80 degrees with respect to the last segment of the primary strut 12a-d, preferably between about 50 and 60 degrees.

Figure 5:
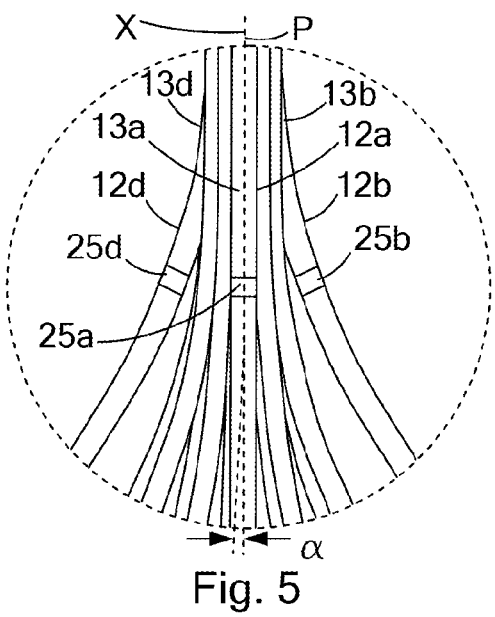
FIG. 5 is an enlarged view of circle 5 in FIG. 2.

As illustrated in FIGS. 5 and 6, each primary strut 12a-d includes a respective axial bend 25a-d. As shown in FIG. 6, each primary strut 12a-d includes a first end 14 which emanates from within the hub 11 and a section 13a-d which extends linearly along a diametric plane between the first end 14 and the axial bend 25a-d. The axial bends 25a-d of the respective primary struts 12a-d result in each primary strut 12a-d being angled by an angle α from a plane defined by the longitudinal axis X and a point along the section 13a-d of that particular primary strut 12a-d. For example, referring to FIGS. 5 and 6, the axial bend 25a of the primary strut 12a is angled from the plane P by an angle α. The plane P is defined by the longitudinal axis X and a point along the section 13a that extends between the first end 14 of the primary strut 12a and the axial bend 25a.

Each proximal portion 20 of each primary strut 12a-d has an axial bend 25a-d formed thereon relative to the longitudinal axis X of the filter 10 and the first end 14, or any point along the section 13a-d, of the respective primary strut 12a-d such that the primary struts 12a-d maintain continuous consistent orientation together when moving between the opened and closed configurations. Thus, as the filter 10 moves between the opened and closed configuration, the primary struts 12a-d maintain a relatively uniform or relatively symmetrical arrangement relative to an end view of the filter. The axial bends 25a-d cause the primary struts 12a-d to close and open relatively consistently, lessening the chance of entanglement. For example (see end view in FIG. 6), the relative arrangement of the primary struts 12a-d is maintained, avoiding crossing over of primary struts 12a-d and thus lessening entanglement thereof.

Referring to FIG. 6, the primary struts 12a-d extend substantially linearly along a diametric plane. However, the axial bend 25a-d on the first curved proximal portion 20 of each primary strut 12a-d results in each primary strut 12a-d extending linearly along a diametric plane from the first end 14 to just before the axial bend 25a-d and from just after the axial bend 25a-d to the second end 15. Thus, the term "substantially linearly," as opposed to merely "linearly," takes into account this slight axial bend 25a-d on each of the respective primary struts 12a-d. While the primary struts 12a-d do not extend completely linearly along a diametric plane due to the slight axial bends 25a-d, they do not extend helically. It is noted that the axial bends 25a-d illustrated in FIG. 6 have been exaggerated for illustration purposes, but may not be so obvious when viewed with the naked eye.

A pair of opposed primary struts, e.g., 12a and 12c in FIG. 6, may be offset by bending the struts 12a and 12c by between about 0.5 degree and 2 degrees relative to plane P to allow the pair of struts 12a and 12c to cross each other relative to the longitudinal axis X. In this embodiment, as best illustrated in FIGS. 5 and 6, the opposed first ends 14 and sections 13a and 13c of respective primary struts 12a and 12c are arranged parallel to one another. Accordingly, the axial bends 25a, 25c are angled with respect to the same plane, plane P, defined by the longitudinal axis X and a point along the section 13a of primary strut 12a and a point along the section 13c of the primary strut 12c.

The same can be said for the pair of opposed primary struts 12b and 12d. As illustrated in FIGS. 5 and 6, the opposed primary struts 12b and 12d are arranged parallel to one another. Accordingly, the axial bends 25b, 25d are angled with respect to the same plane, plane P', defined by the longitudinal axis X and a point along the section 13b of the primary strut 12b and a point along the section 13d of the primary strut 12d. By the offset, the portion of each primary strut 12a-d extending between the respective axial bend 25a-d and the second end of the strut 12a-d is substantially parallel to the corresponding portion of the opposed primary strut 12a-d.

The axial bends 25a-d cause the primary struts 12a-d to be consistently oriented together relative to the longitudinal axis X in each occasion the filter 10 is collapsed in the closed state. Thus, when the filter 10 is loaded in its collapsed configuration and deployed in a body vessel to its expanded configuration, the struts 12a-d expand consistently radially outwardly and remain in relatively the same orientation or arrangement together. As a result, the risk of entanglement of the struts is reduced.

The angle of each axial bend 25a-d may range between about 0.5 and 5°. As the primary struts 12a-d move between the closed state and the expanded state of the filter 10, the second curved distal portions 23 move consistently radially, in a rotating fashion, from the longitudinal axis X toward the vessel wall. The rotating radial movement of the second curved distal portions 23 aid in reducing the risk of entanglement of the primary struts 12a-d.

As best illustrated in FIGS. 2 and 6, the filter 10 includes a plurality of secondary struts 30 having connected ends 32 attached that also emanate from hub 11. Hub 11 attaches by crimping the connected ends 32, along the center point A, of the secondary struts 30 together with the primary struts 12a-d. In this embodiment, each primary strut 12a-d has two secondary struts 30 in side-by-side relationship with the primary strut 12a-d. The secondary struts 30 extend from the connected ends 32 to free ends 34 to centralize the filter 10 in the expanded state in the blood vessel. Preferably, the secondary struts 30 terminate with the free end 34 and without an anchoring hook or a stop member. As shown, each secondary strut 30 extends arcuately along a longitudinal plane and linearly along a diametric plane (see end view in FIG. 6) from the connected end 32 to the free end 34, i.e., the secondary struts 30 do not extend helically.

The secondary struts 30 may be made from the same type of material as the primary struts 12a-d. However, the secondary struts 30 may have a smaller diameter, e.g., at least about 0.012 inches, than the primary struts 12a-d. In this embodiment, each of the secondary struts 30 is formed of a first arc 40 and a second arc 42. As shown in FIG. 2, the first arc 40 extends from the connected end 32 away from the longitudinal axis X and the second arc 42 extends from the first arc 40 towards the longitudinal axis X. As shown, two secondary struts 30 are located on each side of one primary strut 12a-d to form a part of a netting configuration of the filter 10. The hub 11 is preferably made of the same material as the primary struts and secondary struts to minimize the possibility of galvanic corrosion or molecular changes in the material due to welding.

FIG. 6 illustrates the netting pattern including primary struts 12a-d and secondary struts 30 independently spaced substantially equally at their respective planes. For example, the secondary struts 30 may be spaced equally relative to the other secondary struts 30 and the primary struts 12a-d may be spaced equally relative to the other primary struts 12a-d. As a result, the netting pattern in this embodiment shown by the end view of the filter 10 in FIG. 2 (taken along line 6-6) will have uneven or unequal spacing between the primary struts 12a-d and secondary struts 30. However, it is to be understood that the primary and secondary struts 12a-d and 30 may be arranged in any other suitable manner as desired.

When freely expanded, free ends 34 of the secondary struts 30 will expand radially outwardly to a diameter of about 25 mm to 45 mm. For example, the secondary struts 30 may expand radially outwardly to a diameter of between about 35 mm and 45 mm. The second arcs 42 of the free ends 34 engage the wall 51 of a blood vessel 52 to define a second axial plane where the vessel wall 51 is engaged. The secondary struts 30 function to stabilize the position of the filter 10 about the center of the blood vessel 52 in which it is deployed. As a result, the filter 10 has two layers or planes of struts longitudinally engaging the vessel wall 51 of the blood vessel 52. The length of the filter 10 is preferably defined by the length of a primary strut 12a-d.

Furthermore, the diameter of the hub 11 is defined by the size of a bundle containing the primary struts 12a-d and secondary struts 30. In this embodiment, the eight secondary struts 30 minimally add to the diameter of the hub 11 or the overall length of the filter 10, due to the reduced diameter of each secondary strut 30. This is accomplished while maintaining the filter 10 in a centered attitude relative to the vessel wall 51 and formed as a part of the netting configuration of the filter 10. As shown, removal hook 46 extends from hub 11 opposite primary and secondary struts 12a-d and 30.

In this embodiment, each arcuate segment 16 has a thickness of at least about 0.015 inch and a tensile strength of between about 285,000 pounds per square inch (psi) and 330,000 psi. Each anchoring hook 26 is integral with the arcuate segment 16 and has the thickness and the tensile strength of the arcuate segment. Each secondary strut 30 has a thickness of at least about 0.012 inch and a tensile strength of between about 285,000 psi and 330,000 psi.

Figure 7A:
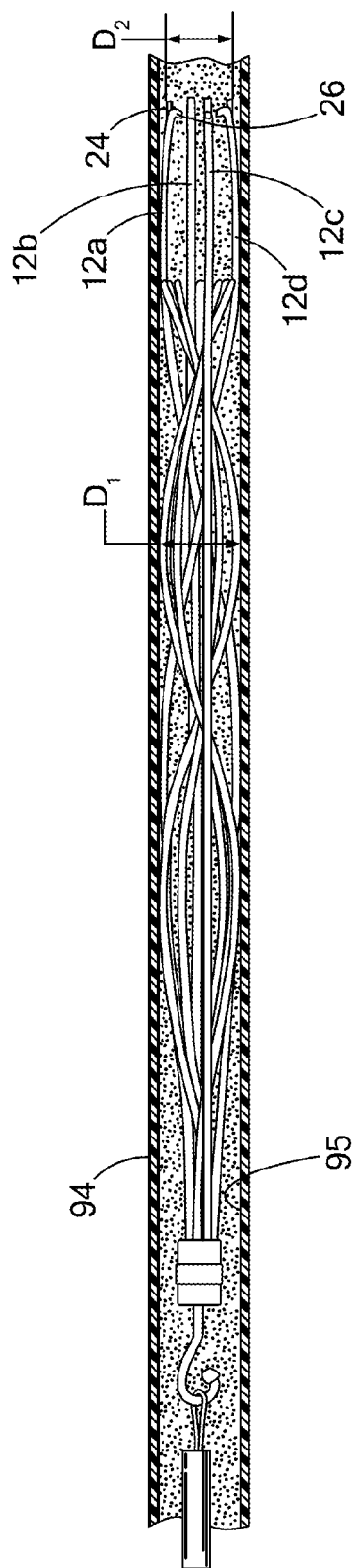
FIG. 7a is a side view of the filter in FIG. 2 in a collapsed state and disposed in an introducer tube.

FIG. 7a illustrates the filter 10 in a collapsed state disposed in a delivery/retrieval tube or sheath 94 for delivery or retrieval. As shown, the filter 10 has primary struts 12a-d, each of which is formed with an axial bend 25a-d for consistent orientation and shaped to cooperate with another primary strut 12a-d along the longitudinal axis X. As a result, shown in the collapsed state in FIGS. 7a and 7b, the anchoring hooks 26 are configured to be inverted or be inwardly positioned along the longitudinal axis X away from the inner wall 95 of the delivery/retrieval sheath 94 and the blood vessel walls for retrieval/delivery of the filter 10. This inverted or inwardly facing configuration of the anchoring hooks 26 allows for simplified delivery and retrieval of filter 10. For example, a concern that the anchoring hooks 26 in the collapsed state may scrape, scratch, or tear the inner wall of a delivery/retrieval tube is eliminated, since the filter 10 of the present invention is shaped to have the anchoring hooks 26 inwardly face each other in the collapsed state. In fact, a set of inner and outer delivery/retrieval sheaths may be eliminated during the delivery or retrieval of the filter 10 through the jugular or femoral vein. Rather, merely one delivery/retrieval tube with a loop snare mechanism may be used to retrieve the filter 10 of the present invention.

With respect to the embodiments of FIGS. 3b-d, the anchoring hooks 226, 326, and 426 are oriented opposite of the respective stop members 224, 324, and 424 such that the anchoring hooks 226, 326, and 426 are curved in a direction toward the hub 11 and toward the respective stop members 224, 324, and 424, and the stop members 224, 324, and 424 extend in a direction away from the hub 11 and toward the respective anchoring hooks 226, 326, and 426. Accordingly, in the collapsed state, the barb extension 328 of the stop member 324 in FIG. 3c and the projecting portion 433 of the stop member 424 in FIG. 3d are configured to be inverted or be inwardly positioned along the longitudinal axis X away from the inner wall 95 of the delivery/retrieval sheath 94 and the blood vessel walls for retrieval/delivery of the respective filters 310 and 410.

Figure 7B:
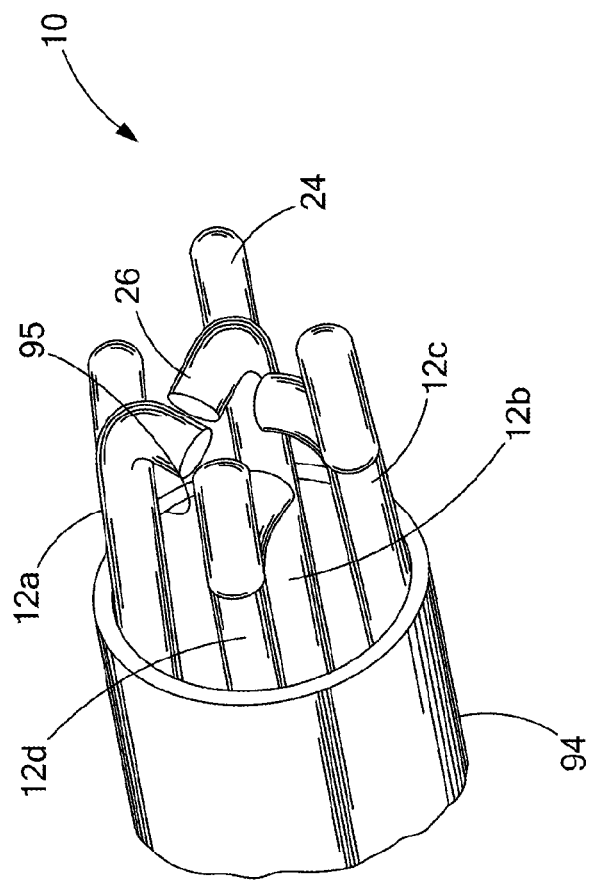
FIG. 7b is an enlarged view of anchoring hooks of the filter in FIG. 2 in the collapsed state.

Moreover, as shown in FIGS. 7a and 7b in the collapsed state, each primary strut 12a-d is configured to cooperate with another primary strut 12a-d along the longitudinal axis X such that the arcuate segments 16, first curved proximal portions 20 or second curved distal portions 23, occupy a first diameter $D_1$. In this embodiment, the first diameter is greater than a second diameter $D_2$ occupied by the anchoring hooks 26 for filter retrieval or delivery. It has been found that the first diameter of the arcuate segments 16 serves to clear a path of retrieval, reducing radial force from the sheath or blood vessel on the anchoring hooks 26 during removal of the filter 10 from a patient. Reducing the radial force on the anchoring hooks 26 assists in preventing the anchoring hooks 26 from scraping, scratching, or tearing the inner wall of a sheath during removal of the filter 10 from a patient.

In this embodiment of the present invention, it is to be noted that the filter 10 may be delivered or retrieved by any suitable introducer (delivery or retrieval) sheath. However, it is preferred that the introducer sheath has an inside diameter of between about 4.5 French and 16 French, and more preferably between about 6.5 French and 14 French.

Figure 8:
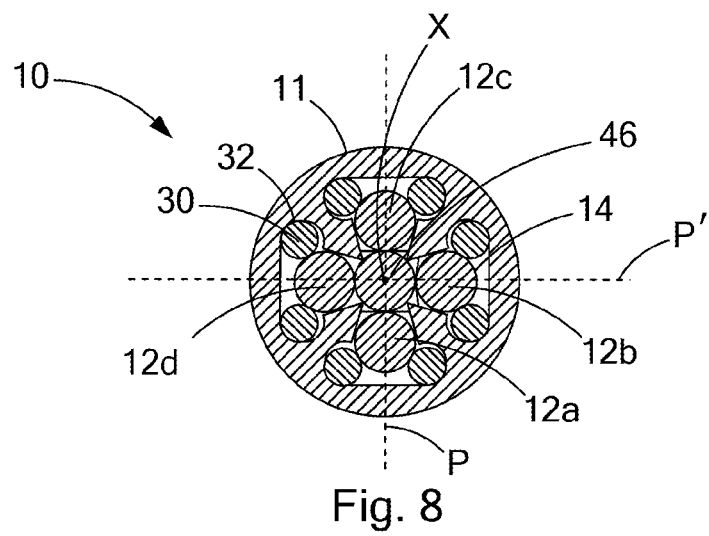
FIG. 8 is a cross-sectional view of a hub of the filter in FIG. 2 taken along line 8-8.

FIG. 8 illustrates a cross-sectional view of the filter 10 of FIG. 2 at hub 11. As shown, the hub 11 houses a bundle of first ends 14 of the four primary struts 12a-d and connected ends 32 of secondary struts 30. FIG. 8 further depicts the configurations of the primary and secondary struts 12a-d and 30. In this embodiment, the primary struts 12a-d are spaced between two secondary struts 30. Of course, the primary struts 12a-d may be spaced between any other suitably desired number of secondary struts 30 without falling beyond the scope or spirit of the present invention.

Figure 9:
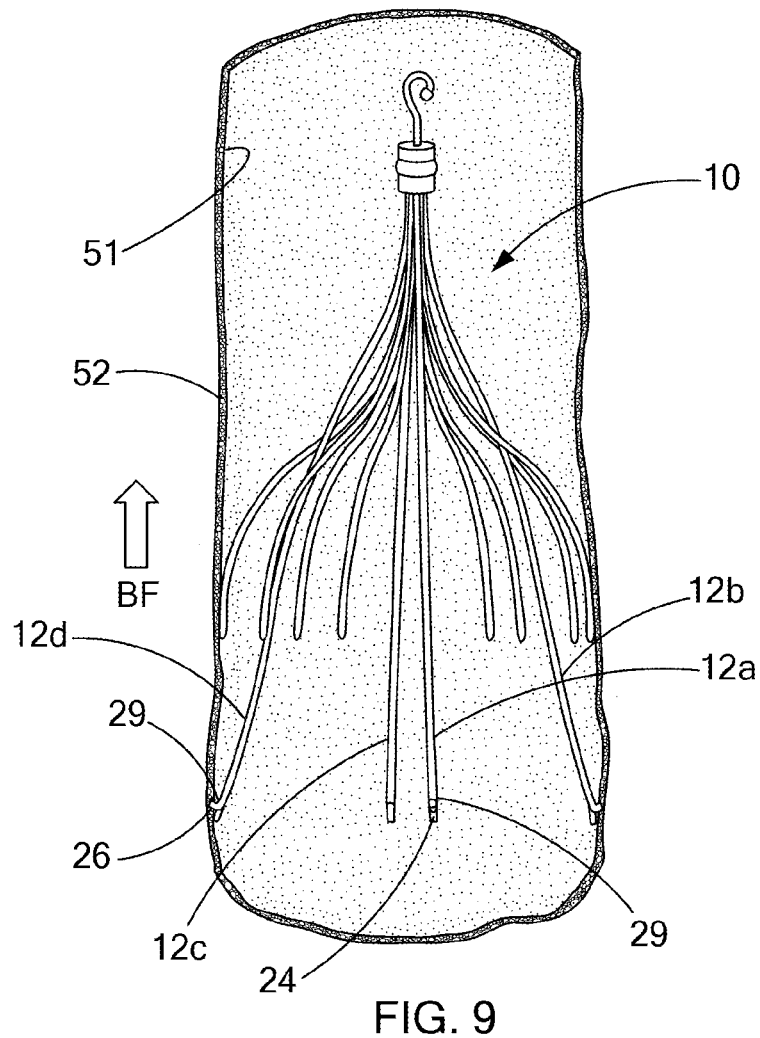
FIG. 9 is a cross-sectional view of the vena cava in which the filter of FIG. 2 has been deployed.

FIG. 9 illustrates the filter 10 fully expanded after being deployed in a blood vessel, for example, the inferior vena cava 52. As shown, the inferior vena cava 52 has been broken away so that the filter 10 can be seen. The direction of the blood flow BF is indicated in FIG. 9, by the arrow that is labeled BF. The anchoring hooks 26 at the ends of the primary struts 12a-d are shown as being anchored in the inner lining of the inferior vena cava 52. The anchoring hooks 26 include barbs 29 that, in one embodiment, project toward the hub 11 of the filter. The barbs 29 function to retain the filter 10 in the location of deployment.

The spring biased configuration of the primary struts 12a-d further causes the anchoring hooks 26 to engage the vessel wall and anchor the filter at the location of deployment. After initial deployment, the pressure of the blood flow on the filter 10 contributes in maintaining the barbs 29 anchored in the inner lining of the inferior vena cava 52. As seen in FIG. 9, the second arcs 42 of secondary struts 30 also have a spring biased configuration to engage with the vessel wall.

As seen in FIG. 9, the hub 11 and removal hook 46 are positioned downstream from the location at which the anchoring hooks 26 are anchored in the vessel. When captured by the struts 12a-d and 30, thrombi remains lodged in the filter. The filter 10 along with the thrombi may then be percutaneously removed from the vena cava. When the filter 10 is to be removed, the removal hook 46 is preferably grasped by a retrieval instrument that is percutaneously introduced in the vena cava in the direction of removal hook 16 first.

Although the embodiments of this invention have been disclosed as being constructed from wire having a round cross section, it could also be cut from a tube of suitable material by laser cutting, electrical discharge machining or any other suitable process.

In the event that the filter has remained in the vessel for a longer period of time, the primary struts may be overgrown by neovascular overgrowth of the intima layer of the vessel wall. The tendency of overgrowing of the struts is increased by the spring biased configuration of the struts and the radial outward orientation of the outer end of the struts in relation to the longitudinal axis. This results in the struts dilating the vessel wall along the contact surface of the struts with the vessel wall. The intima layer overgrowing the struts will increase the anchoring of the filter, so the struts will follow the movements of the wall, and migration of the filter is avoided. Even when the struts are overgrown by intima layer, the filter may be removed without any substantial damage to the vessel wall. The intima layer that has overgrown the struts will restrict the pulling forces to act parallel to the wall and thereby pulling the struts out easily, instead of breaking the overgrown layer. Apart from a small cut caused by the hook, there will not be any further damage and the cut will heal in relatively less time whereas tearing of the intima layer would otherwise take relatively more time to heal.

The filter 10 may be comprised of any suitable material such as superelastic material or spring material, including but not limited to nitinol, stainless steel wire, cobalt-chromium-nickel-molybdenum-iron alloy, or cobalt-chrome alloy. It is understood that the filter 10 may be formed of any other suitable material that will result in a self-opening or self-expanding filter, such as shape memory alloys. Shape memory alloys have a property of becoming rigid, i.e., returning to a remembered state, when heated above a transition temperature. A shape memory alloy suitable for the present invention may comprise Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one alternate embodiment, the filter 10 may be made from Nitinol with a transition temperature that is slightly below normal body temperature of humans, which is about 98.6° F. Although not necessarily a preferred embodiment, when the filter 10 is deployed in a body vessel and exposed to normal body temperature, the alloy of the filter 10 will transform to austenite, that is, the remembered state, which for one embodiment of the present invention is the expanded configuration when the filter 10 is deployed in the body vessel. To remove the filter 10, the filter 10 is cooled to transform the material to martensite which is more ductile than austenite, making the filter 10 more malleable. As such, the filter 10 can be more easily collapsed and pulled into a lumen of a catheter for removal.

In another alternate embodiment, the filter 10 may be made from Nitinol with a transition temperature that is above normal body temperature of humans, which is about 98.6° F. Although not necessarily a preferred embodiment, when the filter 10 is deployed in a body vessel and exposed to normal body temperature, the filter 10 is in the martensitic state so that the filter 10 is sufficiently ductile to bend or form into a desired shape, which for the present invention is an expanded configuration. To remove the filter 10, the filter 10 is heated to transform the alloy to austenite so that the filter 10 becomes rigid and returns to a remembered state, which for the filter 10 in a collapsed configuration.

While the present invention has been described in terms of preferred embodiments, it will be understood, of course, that the invention is not limited thereto since modifications may be made to those skilled in the art, particularly in light of the foregoing teachings.

The invention claimed is:

1. A filter for capturing thrombi in a blood vessel, the filter comprising:

a plurality of struts having a collapsed state for filter retrieval or delivery and an expanded state for engaging with a vessel wall of the blood vessel, the struts having first ends attached together along a longitudinal axis of the filter extending to second ends, each strut including a proximal portion extending from the first end and a distal portion extending from the proximal portion to the second end, the distal portion of each strut terminating in an anchoring hook configured to penetrate the vessel wall; and a stop member connected to each strut of the plurality of struts proximate the anchoring hook, the stop member having a distal tip being configured to engage the vessel wall to prevent further penetration of the anchoring hook into the vessel wall, wherein the stop member enhances visualization of the anchoring hook and its position relative to the vessel wall, wherein the stop member projects radially inward from the strut in a direction towards the longitudinal axis in the expanded state the distal tip is rounded toward the anchoring hook so that it is atraumatic to the vessel wall, the stop member having an outer surface forming an outer distance from the filter strut such that the outer distance decreases towards the first ends.

2. The filter of claim 1, wherein the stop member is formed from a radiopaque material.

3. The filter of claim 1, wherein the stop member includes a plurality of dimples formed on an outer surface thereof.

4. The filter of claim 1, wherein the stop member is formed separately from the strut and attached to the strut by one of welding, soldering, gluing, and crimping.

5. The filter of claim 1, wherein the stop member is disposed proximally relative to the anchoring hook.

6. The filter of claim 5, wherein the stop member projects radially outward from the strut in a direction away from the longitudinal axis in the expanded state.

7. The filter of claim 5, wherein the stop member is disposed a distance in the range of about 2 mm to about 10 mm from the anchoring hook.

8. The filter of claim 5, wherein each strut has a first outer diameter, wherein the stop member includes an annular band having a second outer diameter greater than the first outer diameter.

* * * * *